(12) United States Patent
Pisano et al.

(10) Patent No.: US 7,728,039 B2
(45) Date of Patent: Jun. 1, 2010

(54) BIPHENYL AND NAPHTHYL-PHENYL HYDROXAMIC ACID DERIVATIVES

(75) Inventors: Claudio Pisano, Aprilia (IT); Giuseppe Giannini, Pomezia (IT); Loredana Vesci, Rome (IT); Franco Zunino, Milan (IT); Sabrina Dallavalle, Vimercate (IT); Lucio Merlini, Milan (IT); Sergio Penco, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 219 days.

(21) Appl. No.: 11/993,184

(22) PCT Filed: May 31, 2006

(86) PCT No.: PCT/EP2006/062799

§ 371 (c)(1), (2), (4) Date: Dec. 20, 2007

(87) PCT Pub. No.: WO2007/000383

PCT Pub. Date: Jan. 4, 2007

(65) Prior Publication Data

US 2008/0319082 A1 Dec. 25, 2008

(30) Foreign Application Priority Data

Jun. 28, 2005 (EP) .................. 05013953

(51) Int. Cl.
*A61K 31/185* (2006.01)
*C07C 259/06* (2006.01)
(52) U.S. Cl. ...................... 514/575; 562/621
(58) Field of Classification Search ................ 562/621; 514/575

See application file for complete search history.

(56) References Cited

FOREIGN PATENT DOCUMENTS

| JP | 10 182583 A | 7/1998 |
|---|---|---|
| WO | 03/011808 A | 2/2003 |

OTHER PUBLICATIONS

Garattini et al. (Blood Jan. 1, 2004, 103(1), 194-207).*
Summers et al. (J. Med. Chem. 1987, 30(3), 574-580.*
Mongan et al. Molecular Cancer Therapeutics Mar. 2005, 4(3), 477-486.*

* cited by examiner

*Primary Examiner*—Rebecca L Anderson
*Assistant Examiner*—Jason M Nolan
(74) *Attorney, Agent, or Firm*—Lucas & Mercanti, LLP

(57) ABSTRACT

Biphenyl and phenyl-naphthyl compounds bearing a hydroxamic group, which are endowed with antitumor, and anti-angiogenic activity These compounds are therefore particularly useful for the treatment of drug-resistant tumors.

9 Claims, 2 Drawing Sheets

BIPHENYL AND NAPHTHYL-PHENYL HYDROXAMIC ACID DERIVATIVES

FIELD OF THE INVENTION

The present invention relates to biphenyl and phenyl-naphthyl compounds bearing a hydroxamic group, which are endowed with antitumour, and anti-angiogenic activity

BACKGROUND OF THE INVENTION

The anti-proliferative and anti-angiogenic activity of a few compounds structurally related to the class of the compounds described in the present invention has been reported.

(6-[3'-(1-adamantyl)-4'-hydroxyphenyl]-2-naphthalenecarboxylic acid (AHPN) also named CD437) (Cancer Research, 2002; 62(8), 2430-6; Blood, 2000; 95, 2672-82; Leukemia, 1999, 13, 739-49; Cancer Letters, 1999, 137, 217-2) is reported to be selective for the retinoic acid receptor-gamma RAR-γ, to inhibit cell growth and induces apoptosis in breast carcinoma, melanoma and cervical carcinoma cell lines, including those all trans-retinoic acid- (ATRA-) resistant, with a mechanism independent of receptor binding (WO9703682; J. Med. Chem. 1995, 38, 4993-5006).

In addition, some compounds related to this class of compounds, such as TAC-101 (Clin. Cancer Res. 1999, 5, 2304-10) or derivatives such as RE-80, AM-580 or Am-80 (Eur. J. Pharmacol. 1993, 249, 113-6) have shown antiangiogenic properties.

Novel compounds, which are biphenyl derivatives of acrylic acid have recently been described (Cincinelli R. et al., J. Med. Chem. 2003, 46: 909-912 and WO03/11808). In particular, compound named ST1926 (E-3-(4'-hydroxy-3'-adamantylbiphenyl-4-yl)acrylic acid) was shown to have a potent antiproliferative activity on a large panel of human tumour cells.

One of the last developed analogue of CD437, compound (E)-4-[3'-(1-adamantyl)-4'-hydroxyphenyl]-3-chlorocinnamic acid (3-Cl-AHPC) (Dawson, M. I. et al. J. Med. Chem. 2004, 47(14), 3518-3536; WO0348101) is reported to inhibit the proliferation and to induce apoptosis of cancer cells both in vitro and in vivo.

Patent JP10182583 discloses some phenylcinnamohydroxamic acid derivatives having a differentiating-inducing action on cancer cells and useful as a medicines for treatment of malignant tumours, autoimmune diseases and skin diseases.

DESCRIPTION OF THE INVENTION

The compounds of the present invention are characterised by the presence of a hydroxamic group, which surprisingly confers to the compounds an outstanding antitumour activity. In particular, the compounds of the invention are unexpectedly active on tumour cell lines, which become resistant to other known antitumour compounds, which belong to related chemical classes, but do not contain a hydroxamic group.

Therefore the main object of the present invention is to provide biphenyl and phenyl-naphthyl compounds of Formula (I)

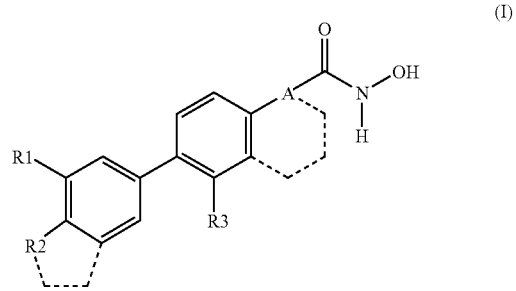

where:
R1 is selected from the group consisting of H, adamantyl, Cl;
R2 is selected from the group consisting of OMe, Cl, CN, and $(CH_2)_nOH$ where n is selected among 0, 1 and 2; or
R2, taken together with the ring to which it is linked, it forms a methylene- or ethylene-dioxy derivative;
R3 is selected between H and Cl;
A is one of the following divalent groups: [CH=CH] (trans), [C≡C], or, taken together with the ring to which it is linked, it forms a naphtyl group.

As already said, the compounds of the present invention show an unexpected antitumour activity on tumour cell lines, which become resistant to other known antitumour compounds.

Preferably they have a resistance index lower than 5, more preferably close to 1. The resistance index is the ratio between the IC50 measured on resistant tumour cell lines and the IC50 measured on sensitive tumour cell lines [(IC50 on resistant tumour cell line/IC50 on sensitive tumour cell line)]; for the determination of this value reference is made to the corresponding section entitled "Biological Studies".

The following are some of the most preferred compounds according to the invention:
E-3-(4'-hydroxy-biphenyl-4-yl)-N-hydroxy-acrylamide (ST2782);
E-3-[3'-(1-adamantyl)-4'-hydroxy-biphenyl-4-yl]-N-hydroxy-acrylamide (ST2992);
6-[3-1-(adamantyl)-4-hydroxyphenyl]-naphthalene-2-carboxylic acid N-hydroxyamide (ST2142);
6-[3-1-(adamantyl)-4-methoxyphenyl]-naphthalene-2-carboxylic acid N-hydroxyamide (ST3259);
3-[4-(8-adamantan-1-yl-2,3-dihydrobenzo[1,4]dioxin-6-yl)-phenyl]-N-hydroxy-acrylamide (ST3081);
E-3-(3'-adamantan-1-yl-2-chloro-4'-hydroxy-biphenyl-4-yl)-N-hydroxy-acrylamide (ST3088);
E-3-(3'-adamantan-1-yl-4'-methoxy-biphenyl-4-yl)-N-hydroxy-acrylamide (ST3056);
E-3-(4'-hydroxymethyl-biphenyl-4-yl)-N-hydroxy-acrylamide (ST3258);
E-3-(3'-chloro-4'-hydroxy-biphenyl-4-yl)-N-hydroxy-acrylamide (ST3192);
E-3-[4'-methoxy-biphenyl-4-yl]-N-hydroxy-acrylamide (ST3595);
E-3-[4'-cyano-biphenyl-4-yl]-N-hydroxy-acrylamide (ST3604); and
E-3-[4'-chlorobiphenyl-4-yl]-N-hydroxy-acrylamide (ST3483).

The experimental results obtained (reported in the section entitled "Examples") show that the compounds of Formula (I), both alone and in combination with other known antitumour drugs, are useful agents for the treatment of tumours.

A further object of the invention described herein are compounds with general Formula (I) and their use in the medical field.

A further object of the invention described herein is a pharmaceutical composition containing as active ingredient a compound of Formula (I) and at least a pharmaceutically acceptable excipient and/or diluent.

A further object of the invention described herein are compounds with general Formula (I) and a process for their preparation.

A further object of the invention described herein is a pharmaceutical composition containing as active ingredient a compound of Formula (I), for the treatment of a tumour pathology, in which the tumour is selected from the group consisting of sarcoma, carcinoma, carcinoid, bone tumour, neuroendocrine tumour, lymphoid leukaemia, acute promyelocytic leukaemia, myeloid leukaemia, monocytic leukaemia, megakaryoblastic leukaemia and Hodgkin's disease.

A further object of the invention described herein is a pharmaceutical composition containing as active ingredient a compound Formula (I), for the treatment of a tumour pathology, in which the tumour has shown drug resistance to the other antitumour agents used for the same treatment.

A further object of the invention described herein is a pharmaceutical composition containing as active ingredient a compound of Formula (I), in combination with one or more known antitumour agents, in which the antitumour compound is selected from the group consisting of alkylating agents, topoisomerase inhibitors, anti-tubulin agents, intercalating compounds, anti metabolites, natural products such as vinca alkaloids, epipodophyllotoxins, antibiotics, enzymes, taxans, and cytodifferentiating compounds.

Among the cytodifferentiating antitumour agents the one preferred is all-trans retinoic acid (ATRA).

A further object of the invention described herein is the use of a compound of Formula (I) for the preparation of a medicine for the treatment of a tumour pathology.

A further object of the invention described herein is the use of a compound of Formula (I) for the preparation of a medicine for the treatment of a tumour pathology in which the tumour has shown drug resistance to the other antitumour drugs used for the same treatment.

A further object of the invention described herein is the use of a compound of Formula (I), in combination with one or more known antitumour agents, for the preparation of a medicine for the treatment of tumour pathologies.

A further object of the invention described herein is the use of a compound of Formula (I) in combination with all-trans retinoic acid for the preparation of a medicine for the treatment of acute promyelocytic leukaemia.

Still another object of the present invention is a process for preparing the pharmaceutical compositions of the invention comprising mixing the active ingredient with at least one pharmaceutically acceptable excipient and/or diluent.

A further object of the present invention is a method of treating a mammal suffering from a tumour pathology, as described above, comprising administering a therapeutically effective amount of the compound(s) of Formula (I).

"Therapeutically effective amount" is an amount effective to achieve the medically desirable result in the treated subject. The pharmaceutical compositions may contain suitable pharmaceutical acceptable carriers, biologically compatible vehicles suitable for administration to an animal (for example, physiological saline) and eventually comprising auxiliaries (like excipients, stabilizers or diluents) which facilitate the processing of the active compounds into preparations which can be used pharmaceutical.

The pharmaceutical compositions may be formulated in any acceptable way to meet the needs of the mode of administration. The use of biomaterials and other polymers for drug delivery, as well the different techniques and models to validate a specific mode of administration, are disclosed in literature.

Modifications of the compounds of the invention to improve penetration of the blood-brain barrier would also be useful.

Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyloleate or triglycerides.

Aqueous injection suspensions that may contain substances increasing the viscosity of the suspension include, for example, sodium carboxymethyl cellulose, sorbitol, and/or dextran. Optionally, the suspension may also contain stabilizers.

Pharmaceutical compositions include suitable solutions for administration by injection, and contain from about 0.01 to 99 percent, preferably from about 20 to 75 percent of active compound together with the excipient. Compositions which can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight.

The compounds of the present invention may be administered to the patient intravenously in a pharmaceutical acceptable carrier such as physiological saline.

Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

As well known in the medical arts, dosages for any one patient depends upon many factors, including the patient's size, body surface area, age, the particular compound to be administered, sex, time and route of administration, general health, and other drugs being administered concurrently.

All references cited herein are entirely incorporated by reference herein, including all data, tables, figures, and text presented in the cited references.

Additionally, the entire contents of the references cited within the references cited herein are also entirely incorporated by reference. Reference to known method steps, conventional method steps, known methods or conventional methods is not in any way an admission that any aspect, description or embodiment of the present invention is disclosed, taught or suggested in the relevant art.

Once understood the features of the methods and products disclosed in present application, the necessity and kind of additional steps can be easily deduced by reviewing prior art, as well as the non-limiting following figures and examples describing the basic details and some applications of the invention The compounds of the present invention can be easily prepared according to a process, which uses as starting material the corresponding carboxylic acid. Such corresponding carboxylic acids can be prepared according to the procedures reported in WO9703682, JP10182583, WO03/11808, and in related publications, or according to standard procedure of organic synthesis.

As an easy reference, the diagrams reported under the section "Examples" can be used and the synthesis of a particular compound of Formula (I) may be easily designed.

The following examples further illustrate the invention, which make reference to the cited Figure.

EXAMPLES

Example 1

Preparation of E-3-(4'-hydroxy-biphenyl-4-yl)-N-hydroxy-acrylamide (ST2782)

Figure 1:
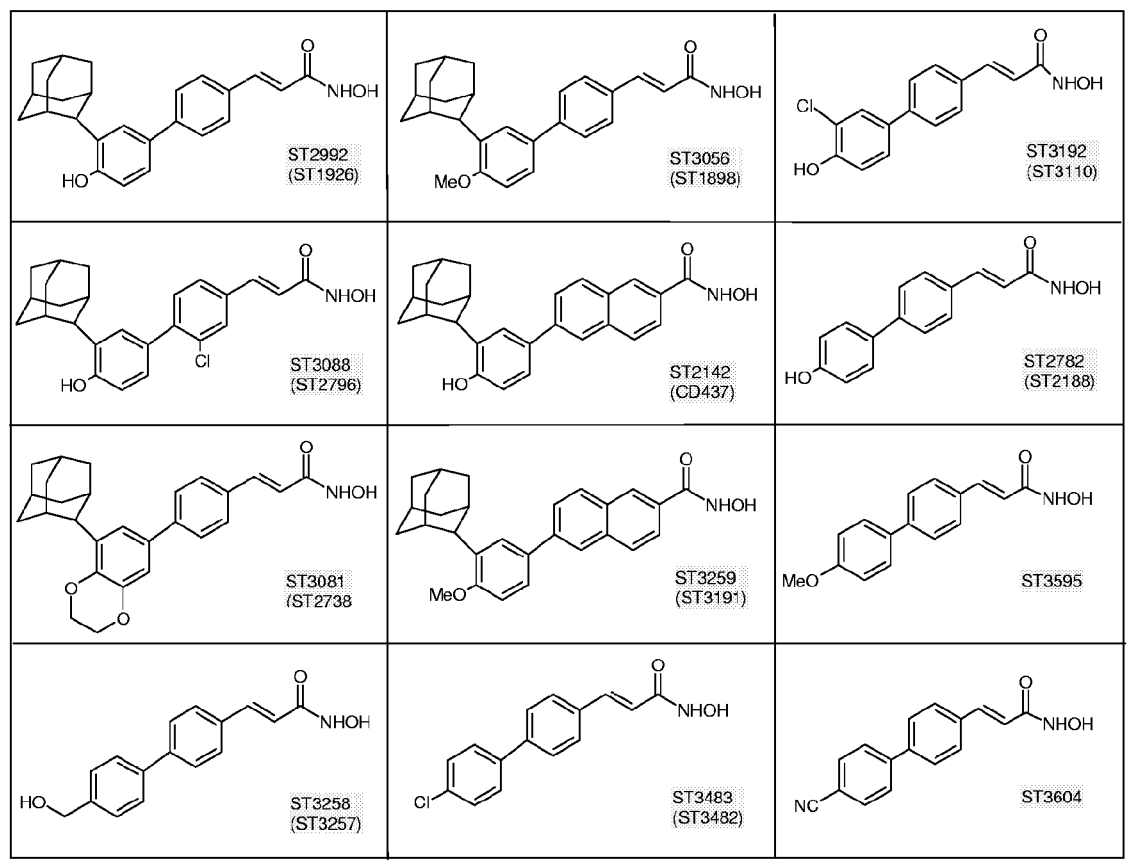
FIG. 1—It shows the chemical structures of the compounds whose synthesis and biological testing has been reported in the present application. The compounds bearing a hydroxamic group are reported with their identification number as indicated in the Examples or Reference Examples and, between brackets, the identification number of the corresponding carboxylic acid compound is reported. The compounds identified by numbers in brackets and their corresponding biological activities data are reported for comparative purposes only.
Figure 2:
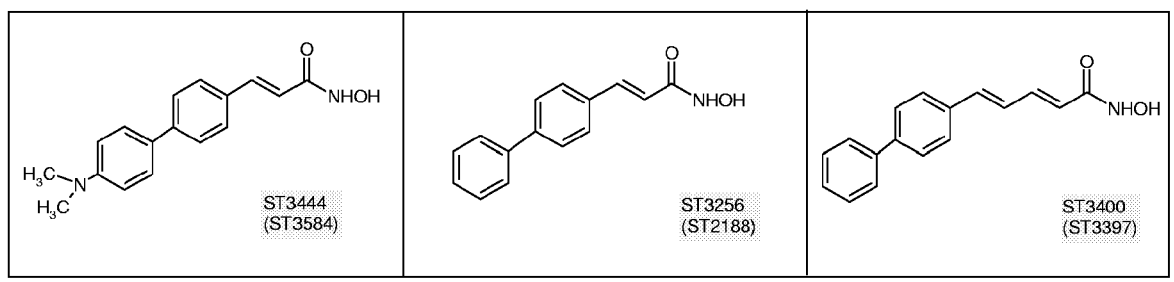
FIG. 2—It shows the chemical structures of the compounds whose biological testing has been reported in the present application, but which are outside the scope of the present invention. The compounds bearing a hydroxamic group are reported with their identification number as indicated in the Examples or Reference Examples and, between brackets, the identification number of the corresponding carboxylic acid compound is reported. The compounds identified by numbers in brackets and their corresponding biological activities data are reported for comparative purposes only.

The title compound was prepared according to synthesis diagram 1 reported as follows.

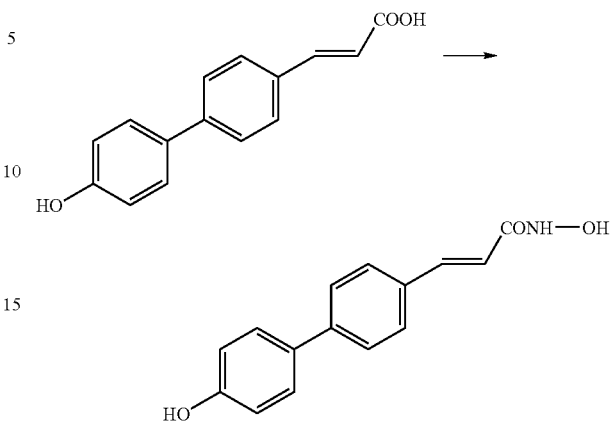

Synthesis diagram 1

250 mg (1.04 mmol) of E-4-(4-hydroxyphenyl)cinnamic acid were dissolved under nitrogen in 10 ml of DMF, then 169 mg (1.25 mmol) of hydroxybenzotriazole hydrate and 259 mg (1.35 mmol) of 1-(3-dimethylaminopropyl)-3-ethyl-carbodiimide hydrochloride were added and the solution thus obtained was kept under stirring at room temperature for 3 hours.

After addition of hydroxylamine hydrochloride (361 mg, 5.2 mmol), followed by 0.72 ml (5.2 mmol) of TEA, the mixture was stirred at room temperature overnight. DMF was removed under reduced pressure and the residue was washed with water to obtain 263 mg of a crude product. Purification by flash chromatography on reverse phase silica gel (LiChroprep RP-18, Merck) using methanol:water 50/50 as eluent afforded 34 mg (13%) of the title compound as a white solid.

M.p. >300° C. $R_f$=0.2 (Merck silica gel 60$F_{254}$, $CH_2Cl_2$:/MeOH 90:10) $R_f$=0.34 (Merck LiChroprep RP-18, MeOH/$H_2O$ 60:40)

$^1$HNMR (DMSO-$d_6$) δ 1.74 (6H, s, 6Ad.); 2.04 (3H, s, 3Ad.); 2.12 (6H, s, 6Ad.); 6.44 (1H, d, —CH═, J=16.00 Hz); 6.82 (2H, d, 2Ar, J=8.19 Hz); 7.43 (1H, d, —CH═, J=16.00 Hz); 7.48-7.69 (5H, m, 5Ar); 9.00 (1H, brs, —CONHOH). 9.62 (1H, s, —OH); 10.73 (1H, brs, —CONHOH).

Example 2

Preparation of E-3-[3'-(1-adamantyl)-4'-hydroxy-biphenyl-4-yl]-N-hydroxy-acrylamide (ST2992)

The title compound was prepared according to the synthesis diagram 2 reported as follows.

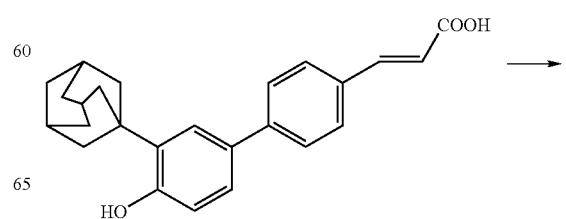

Synthesis diagram 2

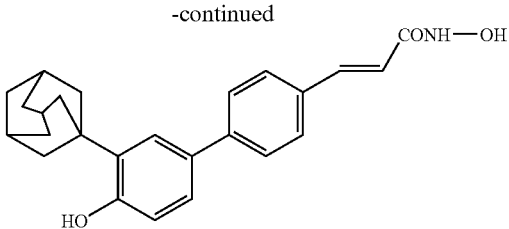

To a solution of E-4-(3-(1-adamantyl)-4-hydroxyphenyl) cinnamic acid (2 g, 5.34 mmol) in 80 ml of DMF were added hydroxybenzotriazole hydrate (866 mg, 5.34 mmol) and 1-(3-dimethylaminopropyl)-3-ethyl-carbodiimide hydrochloride (1130 mg, 6.94 mmol). The mixture was stirred at room temperature for 4 h. After addition of hydroxylamine hydrochloride (1856 mg, 26.7 mmol), followed by 3.7 ml (26.7 mmol) of TEA, the mixture was stirred at room temperature overnight. DMF was removed under reduced pressure and the residue was washed with water to obtain 5 g of a crude product. Purification by flash chromatography on silica gel (phosphate buffered) using as eluent dichloromethane/methanol 95:5 afforded 950 mg of the title compound as a white solid.

M.p. 210-212° C. dec. $R_f$=0.19 (Merck silica gel 60F$_{254}$, Hexane/EtOAc 4:6) $^1$HNMR (DMSO-d$_6$) δ: 1.73 (6H, s, 6Ad.); 2.04 (3H, s, 3Ad.); 2.13 (6H, s, 6Ad.); 6.46 (1H, d, —CH═, J=16.00 Hz); 6.86 (1H, d, 1Ar, J=8.19 Hz); 7.29-7.40 (2H, m, 2Ar); 7.47 (1H, d, —CH═, J=16.00 Hz); 7.52-7.65 (4H, m, 4Ar); 9.03 (1H, brs, —CONHOH); 9.54 (1H, s, —OH); 10.75 (1H, brs, —CONHOH).

Example 3

Preparation of 6-[3-1-(adamantyl)-4-hydroxyphenyl]-naphthalene-2-carboxylic acid N-hydroxyamide (ST2142)

The title compound was prepared according to synthesis diagram 3 reported as follows.

Synthesis diagram 3

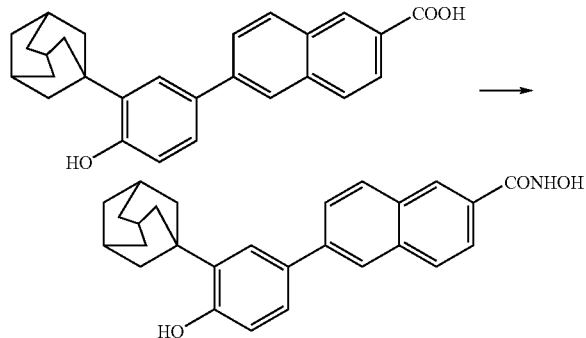

212 mg (0.53 mmol) of 6-[3-1-(adamantly)-4-hydroxyphenyl]-naphtalene-2-carboxylic acid were dissolved under nitrogen in 8 ml of DMF, then 79 mg (0.58 mmol) of hydroxybenzotriazole hydrate and 132 mg (0.67 mmol) of 1-(3-dimethylaminopropyl)-3-ethyl-carbodiimide hydrochloride were added and the solution thus obtained was kept under stirring at room temperature for 2 hours. After addition of hydroxylamine hydrochloride (184 mg, 2.65 mmol), followed by 0.36 ml (2.65 mmol) of TEA, the mixture was stirred at room temperature overnight. DMF was removed under reduced pressure and the residue was washed with water to obtain 150 mg of a crude product. Purification by flash chromatography on reverse phase silica gel (LiChroprep RP-18, MERCK) using methanol:water 85:15 as eluent afforded 80 mg (41%) of the title compound as a white solid.

M.p. 217-219° C. dec.

$^1$HNMR (DMSO-d$_6$) δ: 1.76 (6H, s, 6Ad.); 2.05 (3H, s, 3Ad.); 2.17 (6H, s, 6Ad.); 6.90 (1H, d, 1Ar, J=8.19 Hz); 7.41-7.54 (2H, m, 2Ar); 7.77-7.88 (2H, m, 2Ar); 8.02 (2H, dd, 2Ar, J=2.23, 8.93 Hz); 8.33 (1H, s, 1Ar); 9.57 (1H, brs, —CONHOH); 11.35 (1H, brs, —CONHOH).

Example 4

Preparation of 3-[4-(8-Adamantan-1-yl-2,3-dihydro-benzo[1,4]dioxin-6-yl)-phenyl]-N-hydroxy-acrylamide (ST3081)

The title compound was prepared according synthesis diagram 4 reported as follows.

Synthesis diagram 4

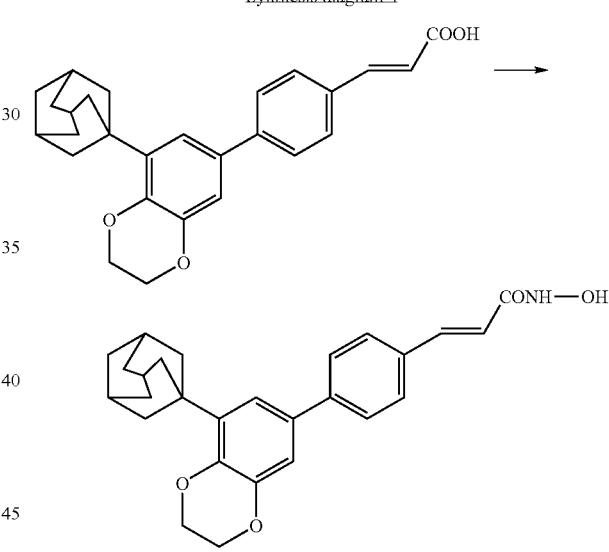

60 mg (0.144 mmol) of 3-[4-(8-(1-adamantyl)-2,3-dihydro-benzo[1,4]dioxin-6yl)-phenyl]-acrylic acid, 55 mg (0.144 mmol) of N-[(dimethylamino)-1H-1,2,3-triazolo-[4,5-b]pyridin-1-yl-methylene]N-methylmethanaminium-hexafluorophosphate N-oxide (HATU) and 50 μL (0.288 mmol) of DIPEA were dissolved under nitrogen in 1 mL of DMF. The resulting mixture was stirred for 2 min. (preactivation time), then hydroxylamine hydrochloride (40 mg, 0.576 mmol) was added. The reaction was stirred at room temperature overnight. After evaporation of the solvent the residue was ice-cooled, added with water and stirred for 1 h at room temperature. The resulting suspension was filtered and the filtrate was washed with water and diethyl ether to afford 40.5 mg (65%) of a white solid.

M.p. 211-213° C. dec. $R_f$=0.6 (Merck silica gel 60F$_{254}$, CH$_2$Cl$_2$/MeOH 9:1))

$^1$HNMR (DMSO-d$_6$) δ: 1.74 (6H, s, 6Ad.); 2.04 (3H, s, 3Ad.); 2.12 (6H, s, 6Ad.); 4.27 (4H, s, CH$_2$—O—); 6.47 (1H, d, —CH═, J=16.00 Hz); 7.00 (1H, s, 1Ar); 7.03 (1H, s, 1Ar);

7.47 (1H, d, —CH═, J=16.00 Hz); 7.52-7.68 (4H, m, 4Ar); 9.04 (1H, brs, —CONHOH); 10.75 (1H, brs, —CONHOH).

Example 5

Preparation of E-3-(3'-Adamantan-1-yl-2-chloro-4'-hydroxy-biphenyl-4-yl)-N-hydroxy-acrylamide (ST3088)

The title compound was prepared according to the synthesis diagram 5 reported as follows.

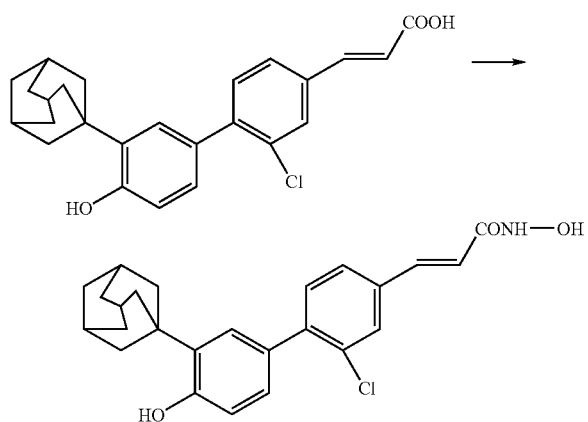

Synthesis diagram 5

5 mg (0.134 mmol) of E-3-[3'-(1-adamantyl)-2-chloro-4'-hydroxybiphenyl-4-yl]-acrylic acid, 51 mg (0.134 mmol) of N-[(dimethylamino)-1H-1,2,3-triazolo-[4,5-b]pyridin-1-yl-methylate]N-methylmethanaminiumhexafluorophosphate N-oxide (HATU) and 47 µL (0.288 mmol) of DIPEA were dissolved under nitrogen in 1 mL of DMF. The resulting mixture was stirred for 2 min. (pre-activation time). Hydroxylamine hydrochloride (37 mg, 0.536 mmol) was added and the reaction was stirred for additional 90 min. After evaporation of the solvent the residue was ice-cooled, added with water and stirred for 1 h at room temperature. The resulting suspension was filtered and the filtrate was washed with water and diethyl ether. The crude was purified by flash chromatography on silica gel (phosphate buffered) using as eluent dichloromethane/methanol 9:1 to obtain 15 mg of a white solid.

M.p. 160° C. dec. $R_f$=0.27 (Merck silica gel 60F$_{254}$, CH$_2$Cl$_2$/MeOH 95:5)

$^1$HNMR (DMSO-d$_6$) δ: 1.72 (6H, s, 6Ad.); 2.02 (3H, s, 3Ad.); 2.09 (6H, s, 6Ad.); 6.51 (1H, d, —CH═, J=16.00 Hz); 6.84 (1H, d, 1Ar, J=8.19 Hz); 7.13 (1H, d, 1Ar, J=8.93 Hz); 7.16 (1H, s, 1Ar); 7.36-7.51 (2H, m, 2Ar); 7.56 (1H, d, 1Ar, J=8.19 Hz); 7.71 (1H, s, 1Ar); 9.10 (1H, brs, —CONHOH); 9.58 (1H, s, —OH); 10.77 (1H, brs, —CONHOH).

Example 6

Preparation of E-3-(3'-Adamantan-1-yl-4'-methoxy-biphenyl-4-yl)-N-hydroxy-acrylamide (ST3056)

The title compound was prepared according to the synthesis diagram 6 reported as follows.

Synthesis diagram 6

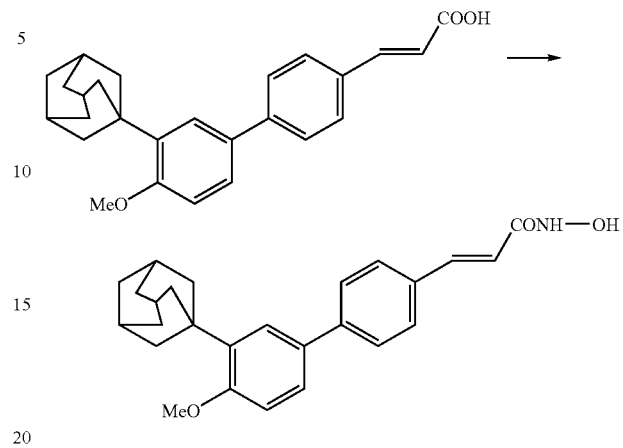

450 mg (1.159 mmol) of E-3-[3'-(1-adamantyl)-2-chloro-4'-methoxybiphenyl-4-yl]-acrylic acid, 529.2 mg (1.392 mmol) of N-[(dimethylamino)-1H-1,2,3-triazolo-[4,5-b]pyridin-1-yl-methylene]N-methylmethanaminiumhexafluorophosphate N-oxide (HATU) and 404 µL (2.32 mmol) of DIPEA were dissolved under nitrogen in 13.5 mL of DMF. The resulting mixture was stirred for 30 min. (pre-activation time). A solution of hydroxylamine hydrochloride (161.19 mg, 2.320 mmol) and DIEA (404 µL, 2.320 mmol) in 4.5 mL of DMF, was added and the reaction was stirred for additional 2.2 h.

Work-up: The reaction mixture was then acidified with aqueous HCl (pH 3-4); the resulting suspension was filtered and the precipitate was washed with aqueous HCl (pH 3-4) and water. It was then suspended in hot MeOH, allowed to cool to room temp. and kept under stirring overnight.

Filtration of resulting suspension and washing with acetone gave 350 mg of white solid (0.867; yield: 75%).

$R_f$=0.27 (Merck silica gel 60F$_{254}$, CH$_2$Cl$_2$/MeOH 90:10)

$^1$HNMR (DMSO-d$_6$) δ: 1.73 (6H, s, 6Ad.); 2.04 (3H, s, 3Ad.); 2.08 (6H, s, 6Ad.); 6.46 (1H, d, —CH═, J=16.11 Hz); 7.05 (1H, d, 1Ar, J=9.07 Hz); 7.35-7.80 (6H, m, Ar); 9.10 (1H, brs, —CONHOH); 9.60 (1H, s, —OH); 10.78 (1H, brs, —CONHOH).

ES-MS: 402.48 [M–H]$^-$ and 426.38 [M–Na]$^+$.

Example 7

Preparation of E-3-(4'-Hydroxy-biphenyl-4-yl)-N-hydroxy-propiolamide

The title compound was prepared following synthesis diagram 7 reported as follows.

Synthesis diagram 7

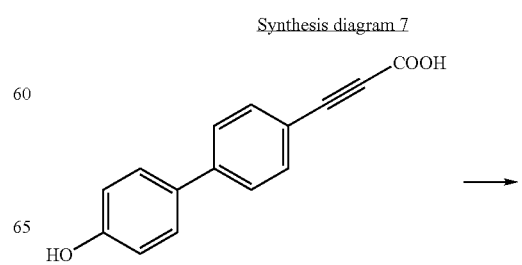

-continued

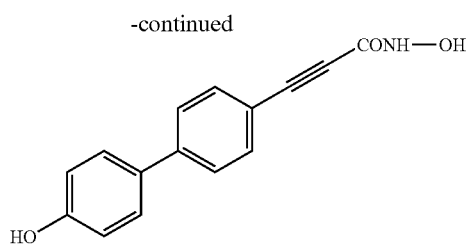

40 mg (0.17 mmol) of (4'-hydroxybiphenyl-4-yl)-propynoic acid were dissolved under nitrogen in 13 μl of DMF, then 1.2 mL of $CH_2Cl_2$ were added and the solution was cooled at 0° C. After slow addition of 33 μL (0.38 mmol) of oxalyl chloride the solution was kept under stirring at 0° C. for 40 min. A solution of mg (0.68 mmol) of hydroxylamine hydrochloride and 148 μL (1.06 mmol) of TEA in 0.7 mL of $THF/H_2O$ 6:1 was dropped at 0° C., then the mixture was stirred at 0° C. for 1.5 h. After addition of $CH_2Cl_2$ the organic layer was washed with HCl 2N, dried with $Na_2SO_4$, filtered and evaporated to obtain 30 mg of a yellow solid.

Purification by flash chromatography on reverse phase ((LiChroprep RP-18, MERCK) using as eluent water/methanol 1:1 afforded 15 mg (35%) of the title compound as a white solid.

$R_f$=0.3 (Merck silica gel 60$F_{254}$, $CH_2Cl_2$:/MeOH 90:10)

$^1$HNMR (DMSO-$d_6$) δ: 6.85 (2H, d, 2Ar, J=8.93 Hz); 7.50 (2H, d, 2Ar, J=8.93 Hz); 7.65-7.85 (4H, m, 4Ar); 9.75 (1H, brs, —CONHOH); 10.50 (1H, brs, —CONHOH).

Example 8

Preparation of E-3-[4'-hydroxymethylbiphenyl-4-yl]-N-hydroxy-acrylamide (ST 3258)

The title compound was prepared following synthesis diagram 8 reported as follows.

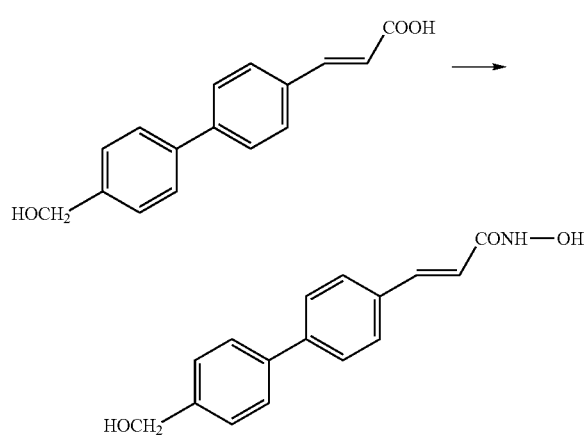

70 mg (0.28 mmol) of E-4-hydroxymethylphenylcinnamic acid were dissolved under nitrogen in 3 ml of DMF, then 107 mg (0.28 mmol) of HATU and 97 μL (0.56 mmol) of DIPEA were added and the solution thus obtained was kept under stirring at room temperature for 5 min. After addition of hydroxylamine hydrochloride (22 mg, 0.31 mmol), the mixture was stirred at room temperature for 3 h. DMF was removed under reduced pressure and the residue was washed with water to obtain, after filtration, 48 mg of a white solid. M.p. 220-223° C. dec. $R_f$=0.6 (Merck silica gel 60$F_{254}$, $CH_2Cl_2$:/MeOH 90:10). $^1$HNMR (DMSO-$d_6$) δ: 4.51 (2H, d, —$CH_2$—, J=5.58 Hz); 5.20 (1H, t, —OH, J=5.58 Hz); 6.47 (1H, d, —CH═, J=16.00 Hz); 7.38 (2H, d, 2Ar, J=7.82 Hz); 7.47 (1H, d, —CH═, J=16.00 Hz); 7.54-7.77 (6H, m, 6Ar); 9.03 (1H, brs, —CONHOH); 10.75 (1H, brs, —CONHOH).

Example 9

Preparation of E-3-[3'-chloro-4'-hydroxybiphenyl-4-yl]-N-hydroxy-acrylamide (ST 3192)

The title compound was prepared following synthesis diagram 9 reported as follows.

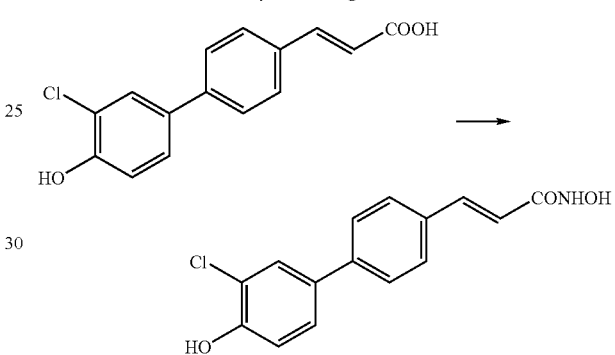

205 mg (0.75 mmol) of E-3-chloro-4-hydroxyphenylcinnamic acid were dissolved under nitrogen in 7.5 ml of DMF, then 285 mg (0.75 mmol) of HATU and 97 μL (0.56 mmol) of DIPEA were added and the solution thus obtained was kept under stirring at room temperature for 2 min. After addition of hydroxylamine hydrochloride (261 mg, 3.75 mmol), the mixture was stirred at room temperature for 2 days. DMF was removed under reduced pressure and the residue was washed with water to obtain, after filtration, 140 mg of a crude product. Purification by flash chromatography on reverse phase ((LiChroprep RP-18, MERCK) using as eluent water/methanol 1:1 and crystallization from diethyl ether afforded 21 mg of the title compound as a white solid. M.p. 172-175° C. $R_f$=0.16 (RP18 MERCK, $H_2O$/MeOH 1:1).

$^1$HNMR (DMSO-$d_6$) δ: 6.48 (1H, d, —CH═, J=15.63 Hz); 7.05 (1H, d, 1Ar, J=8.93 Hz); 7.40-7.74 (7H, m, 7Ar); 9.03 (1H, brs, —CONHOH); 10.50 (1H, brs, —CONHOH).

Example 10

Preparation of 6-[3-1-(adamantyl)-4-methoxyphenyl]-naphthalene-2-carboxylic acid N-hydroxyamide (ST3259)

The title compound was prepared according to synthesis diagram 10 reported as follows.

Synthesis diagram 10

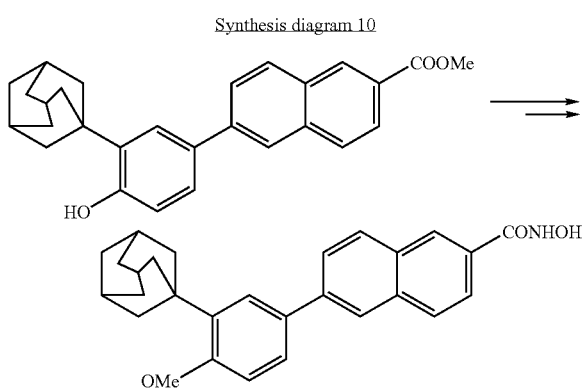

Methyl 6-(3-adamantyl-4-hydroxyphenyl)naphtoate (506 mg, 1.23 mmol) was added to an ice-cooled suspension of NaH (80 mg, 60%) in dry DMF, the mixture stirred 1 h at 0° C., then added with 245 mg (1.7 mmol) of $CH_3I$, and left 90 min at r.t. Taking up with 80 ml of cold water, repeated extraction with $CH_2Cl_2$, then with EtOAc, drying and evaporating the joined organic phases, and chromatography (silicagel, hexane/EtOAc 9/1) gave 300 mg of methyl 6-(3-adamantyl-4-methoxyphenyl)naphtoate. This compound (235 mg) was suspended in a 1M solution of NaOH in MeOH and the mixture was refluxed 8 h. Evaporation, taking up with water, addition of HCl and filtration gave 227 mg of 6-(3-adamantyl-4-methoxyphenyl)naphtoic acid, mp >300° C.

This compound (100 mg, 0.24 mmol) was dissolved under nitrogen in 2.4 ml of DMF, then 92 mg (0.24 mmol) of HATU and 0.2 ml (1.21 mmol) of DIPEA were added and the solution thus obtained was kept under stirring at room temperature for 2 min. After addition of hydroxylamine hydrochloride (84 mg, 1.21 mmol), the mixture was stirred 2 h at r.t. DMF was removed under reduced pressure and the residue was washed with water to obtain, after filtration, 111 mg of crude product, that was purified by flash chromatography (silicagel, MeOH/$H_2O$ 85:15), mp. 222° C., $^1H$ NMR: (DMSO-d6) δ: 1.76 (s, 6H, Adam.), 2.03 (s, 3H, Adam), 2.14 (s, 6H, Adam), 3.86 (s, 3H, OCH3), 7.12 (d, 1H, 1Ar, J=8.56), 7.57 (d, 1H, 1Ar, J=1.86), 7.65 (dd, 1H, 1Ar, J=1.86, 8.93), 7.83 (dd, 1H, 1Ar, J=8.56, 1.86), 7.88 (dd, 1H, 1Ar, J=8.56, 1.86), 8.00-8.10 (m, 2H, 2Ar), 8.19 (s, 1H, 1Ar), 8.35 (s, 1H, 1Ar), 9.40 (s, 1H), 11.35 (s, 1H).

Example 11

Preparation of E-3-[4'-chlorobiphenyl-4-yl]-N-hydroxy-acrylamide (ST3483)

The title compound was prepared according to synthesis diagram 11 reported as follows.

Synthesis diagram 11

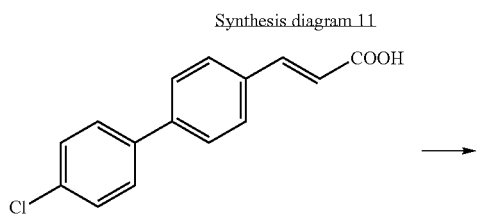

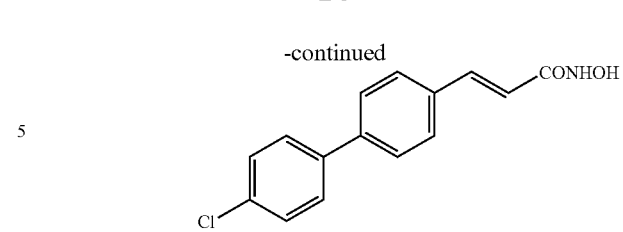

To a mixture of 61 mg (0.22 mmol) of 3-(4-chlorobiphenylyl)acrylic acid and 26 mg (0.22 mmol) of O-tetrahydropyranylhydroxylamine in 3 ml of THF were added 0.45 ml (0.46 mmol) of lithium hexadimethylsilazane, the mixture was stirred 10 min under nitrogen, then the reaction was quenched with $NH_4Cl$ solution. Once at room temperature, the mixture was extracted with EtOAc, and the extract evaporated to give 79 mg of 2-tetrahydropyranyloxyamide of 3-(4-chlorobiphenylyl)acrylic acid. This compound (79 mg, 0.22 mmol) was dissolved in 3 ml of MeOH, added with 12 mg (0.066 mmol) of p-toluenesulfonic acid monohydrate, and the mixture was stirred 2 days at room temp. Filtration and washing with MeOH gave the hydroxyamide of 3-(4-chlorobiphenylyl)acrylic acid, mp. 200-202° C., $R_f$=0.6 (TLC Merck silicagel, $CH_2Cl_2$/MeOH 95/5), $^1H$ NMR (DMSO-$d_6$) δ: 6.50 (s, 1H, —CH=, J=16.00 Hz), 7.49 (s, 1H, —CH=, J=16.00 Hz), 7.50-7.75 (m, 8H, 8Ar), 9.10 (s, 1H), 10.50 (s, 1H).

Example 12

Preparation of E-3-[4'-methoxy-biphenyl-4-yl]-N-hydroxy-acrylamide (ST3595)

The title compound was prepared according to synthesis diagram 12 reported as follows.

Synthesis diagram 12

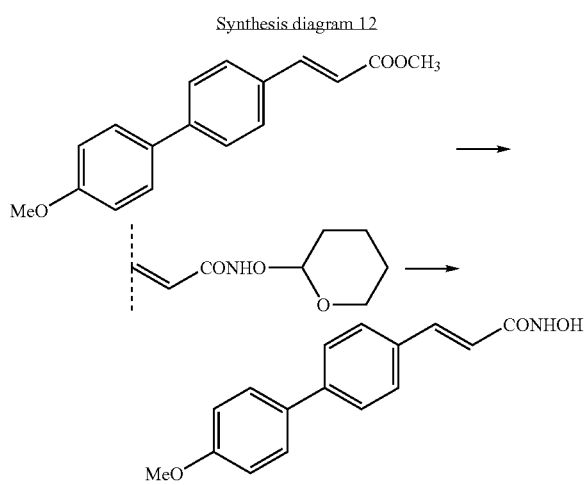

200 mg (0.83 mmol) of methyl 4-bromocinnamate were dissolved in dry toluene, added with 29 mg (0.025 mmol) of Pd(PPh$_3$)$_4$, a solution of 152 mg (0.91 mmol) of 4-methoxybenzeneboronic acid in 0.5 ml of EtOH, 1.66 ml of 2M $Na_2CO_3$ in water, and refluxed 2 h. Addition of EtOAc, washing with water, then with brine, filtration and flash chromatography (Merck silicagel) with Hexane/EtOAc mixtures from 95/5 to 8/2 gave 112 mg of methyl 3-(4-methoxybiphenylyl)acrylate, mp. 175-177° C.

A solution of the above compound (110 mg, 0.41 mmol) and of 2-tetrahydropyranyl-O-hydroxylamine (48 mg, 0.41 mmol) in 6 ml THF was cooled at −78° C., added with 0.81 ml of sodium hexamethyldisilazane, stirred 2 hrs, then heated at −20° C., cooled again at −78° C., quenched with NH₄Cl, extracted with AcOEt, the extrac evaporated to give 145 mg of 2-tetrahydropyranyloxyamide of 3-(4-methoxybiphenylyl) acrylic acid, as a yellow solid.

A solution of the above compound (145 mg, 0.41 mmol) in 5 ml of MeOH was treated with 23 mg (0.12 mmol) of p-toluenesulfonic acid, stirred 24 h at room temp, filtered and washed with MeOH, to give 50 mg of 3-(4-methoxybiphenylyl)acrylic acid hydroxyamide, mp. 199° C. (dec), Rf 0.2 (CH$_2$Cl$_2$/MeOH 95/5), $^1$H NMR: (DMSO-d$_6$): 3.80 (s, 3H, OMe), 6.47 (d, 1H, —CH═, J=15.6 Hz), 7.03 (d, 2H, 2Ar, J=8.9 Hz), 7.48 (d, 1H, CH═, J=15.6 Hz), 7.56-7.73 (m, 6H, 6Ar), 9.05 (s, 1H), 10.76 (s, 1H).

Example 13

Preparation of E-3-[4'-cyano-biphenyl-4-yl]-N-hydroxy-acrylamide (ST3604)

The title compound was prepared according to synthesis diagram 13 reported as follows.

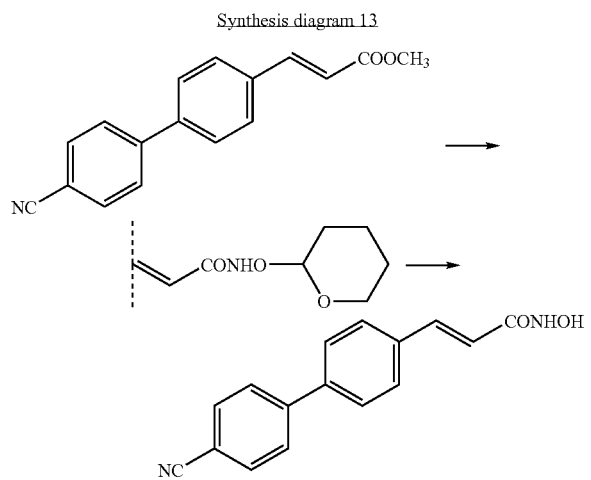

Synthesis diagram 13

820 mg (3.4 mmol) of methyl 4-bromocinnamate were dissolved in 7 ml of dry toluene, added with 116 mg (0.1 mmol) of Pd(PPh$_3$)$_4$, a solution of 374 mg (1.1 mmol) of 4-cyanobenzeneboronic acid in 2 ml of MeOH, 6.8 ml of 2M Na$_2$CO$_3$ in water, and refluxed 9 h. Addition of EtOAc, washing with water, then with brine, filtration and flash chromatography (Merck silicagel) with Hexane/EtOAc mixtures 9/1 gave 273 mg of methyl 3-(4-cyanobiphenylyl)acrylate, mp. 150-152° C.

A solution of the above compound (270 mg, 1.02 mmol) and of 2-tetrahydropyranyl-O-hydroxylamine (117 mg, 1.02 mmol) in 14 ml THF was cooled at −78° C., added with 1.07 ml of sodium hexamethyldisilazane, stirred 2 hrs, then heated at −20° C., cooled again at −78° C., quenched with NH4Cl, extracted with AcOEt, the extract evaporated and chromatographed (Merck silicagel) with Hexane/EtOAc 6/4 to give 189 mg of 2-tetrahydropyranyloxyamide of 3-(4-cyanobiphenylyl)acrylic acid, as a white solid, mp. 211-213° C.

A solution of the above compound (187 mg, 0.54 mmol) in 5 ml of MeOH was treated with 30 mg (0.16 mmol) of p-toluenesulfonic acid, stirred 24 h at room temp, filtered and washed with MeOH, to give 96 mg of 3-(4-cyanobiphenylyl) acrylic acid hydroxyamide, mp. 212-214° C., R$_f$ 0.3 (CH$_2$Cl$_2$/MeOH 95/5), $^1$H NMR: (DMSO-d$_6$): 6.54 (d, 1H, —CH═, J=15.3 Hz), 7.51 (d, 1H, CH═, J=15.3 Hz), 7.69 (d, 2H, 2Ar, J=8.2 Hz), 7.82 (d, 2H, 2Ar, J=8.2 Hz), 7.8-8.0 (m, 4H, 6Ar), 9.05 (s, 1H, NH), 10.80 (s, 1H, OH).

REFERENCE EXAMPLES

In this section we report the synthesis of some compounds, which have been synthesized and tested for comparative purposes, in order to show the superiority and the advantages of the claimed compounds over their closest homologues.

Reference Example 1

Preparation of N-hydroxy-3-(4'-hydroxybiphenyl-4-yl)-proprionamide (ST 3208)

The title compound was prepared following synthesis diagram 1R reported as follows.

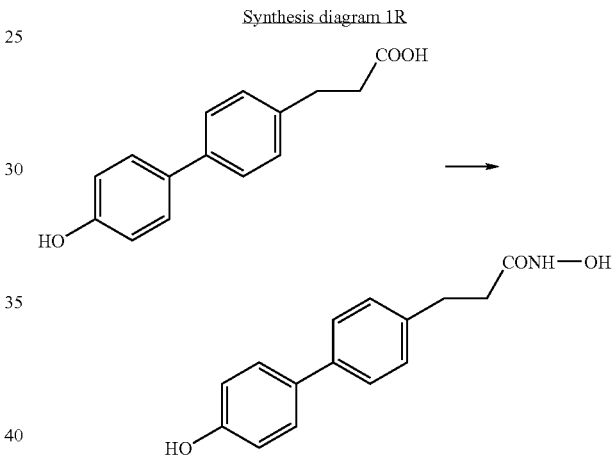

Synthesis diagram 1R 368 mg (1.5 mmol) of 3-(4'-hydroxybiphenyl-4-yl)-propionic acid were dissolved under nitrogen in 15 ml of DMF, then 568 mg (1.5 mmol) of HBTU and 1.23 ml (7.5 mmol) of DIPEA were added and the solution thus obtained was kept under stirring at room temperature for 10 min. After addition of hydroxylamine hydrochloride (521 mg, 7.5 mmol), the mixture was stirred at room temperature for 3.5 h. DMF was removed under reduced pressure, the residue added with water and stirred at 0° C. for 15 min. to obtain, after filtration, 354 mg of a white solid (92%). M.p. 180-182° C. R$_f$=0.1 (Merck silica gel 60F$_{254}$, CH$_2$Cl$_2$:/MeOH 95:5)

$^1$HNMR (DMSO-d$_6$) δ: 2.27 (2H, d, —CH$_2$—, J=7.82 Hz); 2.81 (2H, d, —CH$_2$—, J=7.82 Hz); 6.82 (2H, d, 2Ar, J=8.93 Hz); 7.22 (2H, d, 2Ar, J=8.19 Hz); 7.40-7.55 (4H, m, 4Ar); 8.75 (1H, brs, —CONHOH); 9.55 (1H, brs, —CONHOH); 10.45 (1H, brs, —OH).

Reference Example 2

Preparation of E-3-(biphenyl-4-yl)-N-hydroxy-acrylamide (ST3256)

The title compound was prepared following synthesis diagram 2R reported as follows.

Synthesis diagram 2R

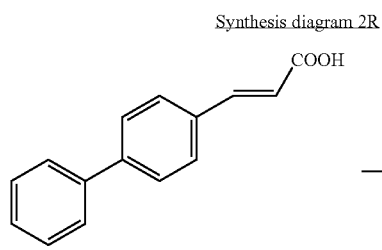

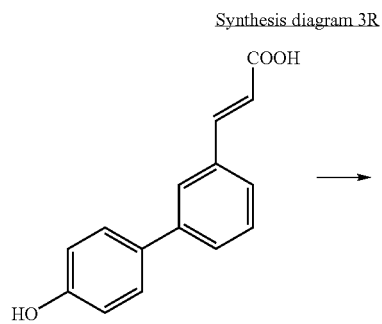

200 mg (0.89 mmol) of E-4-phenylcinnamic acid were dissolved under nitrogen in 9 ml of DMF, then 338 mg (0.89 mmol) of HATU and 308 µL (1.78 mmol) of DIPEA were added and the solution thus obtained was kept under stirring at room temperature for 2 min. After addition of hydroxylamine hydrochloride (68 mg, 0.98 mmol), the mixture was stirred at room temperature for 4 h. DMF was removed under reduced pressure and the residue was washed with water to obtain, after filtration, 220 mg of a white solid.

M.p. >168-170° C. $R_f$=0.6 (Merck silica gel 60F$_{254}$, CH$_2$Cl$_2$:/MeOH 90:10) $^1$HNMR (DMSO-d$_6$) δ 6.48 (1H, d, —CH=, J=16.00 Hz); 6.30-7.75 (10H, m, 9Ar+—CH=); 9.05 (1H, brs, —CONHOH). 10.50 (1H, brs, —CONHOH).

Reference Example 3

Preparation of E-3-[4'-hydroxybiphenyl-3-yl]-N-hydroxyacrylamide (ST3284)

The title compound was prepared following synthesis diagram 3R reported as follows.

Synthesis diagram 3R

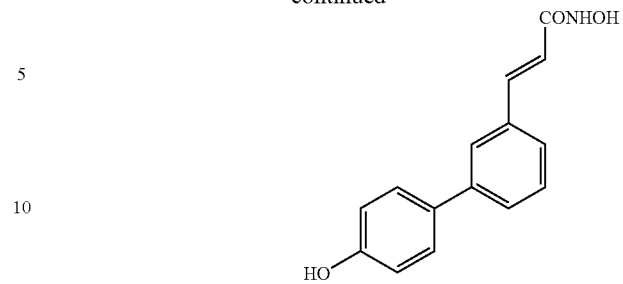

70 mg (0.29 mmol) of E-3-(4'-hydroxybiphenyl-3-yl)-acrylic acid were dissolved under nitrogen in 3 ml of DMF, then 109 mg (0.29 mmol) of HBTU and 100 µL (0.57 mmol) of DIPEA were added at 0° C. After 5 min hydroxylamine hydrochloride (20 mg, 0.29 mmol) was added and the mixture was stirred at 0° C. for 10 min., then at room temperature for 4 h. DMF was removed under reduced pressure and the residue was washed with water to obtain, after filtration, 73 mg of a crude product. Purification by flash chromatography on KH$_2$PO$_4$ buffered silicagel using as eluent CH$_2$Cl$_2$/MeOH 95:5 afforded 24 mg of the title compound as a white solid. M.p. 127-128° C. $R_f$=0.26 (Merck silica gel 60F$_{254}$, CH$_2$Cl$_2$:/MeOH 90:10)

$^1$HNMR (DMSO-d$_6$) δ: 6.51 (1H, d, —CH=, J=16Hz); 6.85 (2H, d, 2Ar, J=8.93 Hz); 7.35-7.80 (7H, m, 6Ar+—CH=); 9.03 (1H, brs, —CONHOH); 9.60 (1H, brs, —OH); 10.50 (1H, brs, —CONHOH).

Reference Example 4

Preparation of E,E-5-biphenylyl-pentadienoic acid N-hydroxyamide (ST3400)

The title compound was prepared according to synthesis diagram 4R reported as follows.

Synthesis diagram 4R

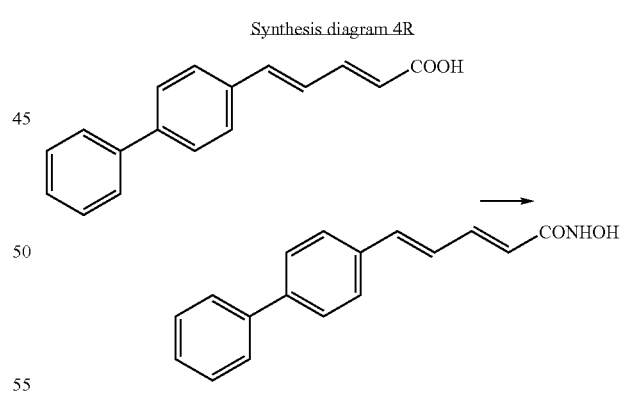

168 mg (0.7 mmol) of E,E-5-biphenylyl-pentadienoic acid (prepared according to L. M. Werbel et al. J. Med. Chem. 10, 366 (1967)) were dissolved under nitrogen in 7 ml of DMF, then 267 mg (0.7 mmol) of HBTU and 245 µL (0.56 mmol) of DIPEA were added and the solution thus obtained was kept under stirring at room temperature for 10 min. After addition of hydroxylamine hydrochloride (54 mg, 0.77 mmol), the mixture was stirred at room temperature overnight. DMF was removed under reduced pressure and the residue was washed with water to obtain, after filtration, 53 mg of product. $^1$H NMR: (DMSO-d$_6$) δ: 6.02 (s, 1H, —CH=, J=14.89 Hz), 6.90-7.40 (m, 3H), 7.40 (m, 1H, 1Ar), 7.45-7.50 (m, 2H, 2Ar), 7.60-7.75 (m, 6H, 6Ar), 9.00 (s, 1H), 10.75 (s, 1H).

Reference Example 5

Preparation of E-3-[4'-dimethylaminobiphenyl-4-yl]-N-hydroxy-acrylamide (ST3444)

The title compound was prepared according to synthesis diagram 5R reported as follows.

Synthesis diagram 5R

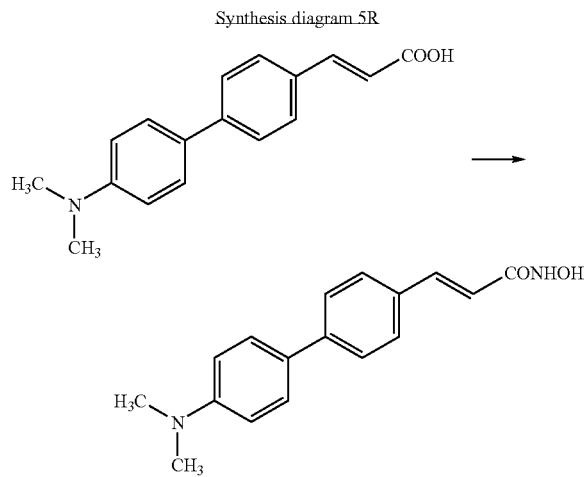

35 mg (0.13 mmol) of E-4-(4-dimethylaminophenyl)cinnamic acid (prepared by Suzuki reaction of 4-dimethylamino-bromobenzene with methyl 4-bromocinnamate followed by hydrolysis of the ester) were dissolved under nitrogen in 1.3 ml of DMF, then 55 mg (0.14 mmol) of HBTU and 43 µL (0.26 mmol) of DIPEA were added and the solution thus obtained was kept under stirring at room temperature for 10 min. After addition of hydroxylamine hydrochloride (10 mg, 0.14 mmol), the mixture was stirred at room temperature overnight. DMF was removed under reduced pressure and the residue was washed with water to obtain, after filtration, drying and taking up with ether, 25 mg of product, m.p. 260-263° C. (dec). $^1$H NMR: (DMSO-$d_6$) δ: 2.95 (s, 6H, N(CH$_3$)$_2$), 6.44 (s, 1H, —CH═, J=16.38 Hz), 6.80 (d, 2H, 2Ar, J=8.93 Hz), 7.46 (d, 1H, CH═, J=16 Hz), 7.52-7.70 (m, 6H, 6Ar), 9.00 (s, 1H), 10.75 (s, 1H).

Biological Studies

Cytotoxicity Results

The cytotoxic effect of some biphenyl and phenylnaphthyl compounds bearing a hydroxamic acid group is reported herein. These molecules possess distinctive pharmacological features from the corresponding compounds bearing a carboxylic acid group. The chemical structures of the tested compounds of the invention and of the corresponding compounds bearing a carboxylic acid group are reported in FIG. 1. To test the effects of the compounds on cell growth, NB4 human promyelocytic leukaemia, NCI-H460 non-small cell carcinoma cells, H460/(R9A) (resistant to carboxylic acid-bearing compounds: ST1898, ST1926, ST1964), HCT-116 human colon carcinoma cells, IGROV-1 and IGROV-1/Pt (sensitive ovarian carcinoma and platinum-resistant ovarian carcinoma cells, respectively) were used. NB4 and NCI-H460 tumour cells were grown in RPMI 1640 containing 10% foetal bovine serum (GIBCO), HCT-116 tumour cells were grown in McCoy's 5A containing 10% foetal bovine serum (GIBCO), IGROV-1 and IGROV-1/Pt were grown in DMEM containing 10% foetal bovine serum (GIBCO), Tumour cells were seeded in 96-well tissue culture plates at approximately 10% confluence and were allowed to attach and recover for at least 24 h. Varying concentrations of the drugs were then added to each well to calculate their IC50 value (the concentration which inhibits the 50% of cell survival). The plates were incubated for 24 h at 37° C. At the end of the treatment, for NB4 tumour cells in suspension, the procedure was performed as follows: medium culture was removed by centrifugation of the plates at 1600×g for 10 min and the surnatant was removed. 250 µl PBS were added, then the plates were centrifuged at 1600×g for 10 min, the surnatant was removed. 200 µl/well of medium culture RPMI 1640 containing 10% FCS were added and the plates were incubated at 37° C. for other 48 h. The plates were centrifuged again at 1600×g for 10 min, the medium culture was removed and 200 µl PBS and 50 µl of cold 80% TCA were added. The plates were incubated on ice for at least 1 h. TCA was removed, the plates were washed 3 times for immersion in distilled-water and dried on paper and at 40° C. for 5 min. Then 200 µl of 0.4% sulphorodamine B in 1% acetic acid were added. The plates were incubated at room temperature for other 30 min. Sulphorodamine B was removed, the plates were washed for immersion in 1% acetic acid for 3 times, then they were dried on paper and at 40° C. for 5 min. Then 200 µl Tris 10 mM were added, the plates were kept under stirring for 20 min. The survival cell was determined as optical density by a Multiskan spectrofluorimeter at 540 nm. For the tumour cells in adhesion (NCI-H460 and HCT-116), the procedure was as above mentioned, except that at the end of the treatment, the plates were washed by remotion of the surnatant and addition of PBS 3 times without centrifugation. Also the last day of the assay, the surnatant was removed without centrifugation.

The amount of cells killed was calculated as the percentage decrease in sulphorodamine B binding compared with control cultures. The IC$_{50}$ values (the concentration which inhibits the 50% of cell survival) were calculated with the "ALLFIT" program.

The resistant tumour cell line NCI H460 R9A was a clone selected for the resistance to ST1926 (Table 3). To obtain the resistant tumour cell line, the sensitive NCI-H460 tumour cells were treated with 2 µM ST1926 for 24 hours and maintained in drug-free medium for a recovering time of 7 days. Then, survived cells were cultured applying a continuous selective pressure of 2 µM (10×IC$_{50}$) ST1926. Resistant NCI-H460 cells were subculture for 3-4 times before increasing ST1926 concentration to 4 µM (20×IC$_{50}$). Survived cells were seeded in 96-well plates to isolate resistant cells clones and maintained in complete medium with 4 µM of ST1926. The tumour cell line was maintained at least for one week, before seeding for SRB cytotoxicity assay, in drug-free medium.

Surprisingly, the hydroxamic derivatives ST2782 and ST3056 showed, with respect the corresponding compounds bearing a carboxylic acid group (ST2188 and ST1898 respectively), an improved anti-proliferative activity on different tumour cell lines (Table 1). The difference in the activity becomes impressive for ST2782 when compared with ST2188.

TABLE 1

Cytotoxicity of different compounds on NB4. IGROV-1 and IGROV-1/Pt tumour cells

| Compound | NB4 | IGROV-1 | IGROV-1/Pt |
|---|---|---|---|
| | | IC50 ± SD, µM | |
| ST2188 | 78.7 ± 7.4 | 89 ± 11 | 156 ± 2 |
| ST2782 | 2.3 ± 0.02 | 8.8 ± 3 | 7.7 ± 1.6 |
| ST1898 | 1.1 ± 0.07 | 1.19 ± 0.05 | 1.43 ± 0.05 |
| ST 3056 | 0.60 ± 0.05 | 0.96 ± 0.03 | 1.79 ± 0.07 |

In addition, the hydroxamic derivatives, ST2782, ST2992, ST3081, ST3088, ST3056, ST2142 revealed a significant antiproliferative activity on different tumour cells (Table 2).

TABLE 2

Cytotoxicity of different compounds on NCI-H460, HCT-116, IGROV-1 and IGROV-1/Pt tumour cells

| Compound | NCI-H460 | HCT-116 | IGROV-1 | IGROV-1/Pt |
|---|---|---|---|---|
| | | IC50 ± SD, µM | | |
| ST2992 | 1.2 ± 0.03 | 3.0 ± 0.2 | 0.77 ± 0.05 | 0.55 ± 0.05 |
| ST2142 | 1.0 ± 0.06 | 2.9 ± 0.2 | 0.65 ± 0.1 | 1.1 ± 0.03 |
| ST 3056 | 0.62 ± 0.04 | 1.3 ± 0.1 | 0.96 ± 0.03 | 1.79 ± 0.07 |
| ST 3081 | 1.0 ± 0.04 | 2.55 ± 0.03 | 1.22 ± 0.04 | 0.84 ± 0.02 |
| ST2782 | 6.0 ± 0.9 | 6.7 ± 0.7 | 8.8 ± 3 | 7.7 ± 1.6 |
| ST 3088 | 5.4 ± 0.3 | 5.4 ± 0.9 | 1.34 ± 0.04 | 1.61 ± 0.1 |

Surprisingly, these compounds were also effective as cytotoxic agents on a lung carcinoma cell line H460/(R9A) selected for its resistance to compounds bearing a carboxylic acid group (ST1898, ST1926, ST1964).

To evaluate the effect of the compound on survival cells, the sulphorodamine B test was used. The amount of cells killed was calculated as the percentage decrease in sulphorodamine B binding compared with control cultures. The $IC_{50}$ values (the concentration which inhibits the 50% of cell survival) were calculated with the "ALLFIT" program.

As shown in Table 3, while the corresponding compounds bearing carboxylic acid groups, e.g. ST1926, ST1964 (CD437), ST1898 were 34-78 fold less effective on H460/R9A, the hydroxamic derivatives e.g. ST2142, ST2992, ST3056, completely overcame the resistance, thus confirming that the selected compounds had specific pharmacological differences from the corresponding carboxylic compounds. Interestingly, the same characteristic are retained by ST2782, ST3081 and ST3088.

TABLE 3

Citotoxicity of different compounds on NCI-H460, NCI-H460 R9A tumour cells

| Compound | NCI-H460 | NCI-H460 R9A | RI |
|---|---|---|---|
| | IC50 ± SD, µM | | |
| ST1926 | 0.13 ± 0.01 | 10.1 ± 0.7 | 77.7 |
| ST2992 | 1.2 ± 0.03 | 1.2 ± 0.1 | 1.0 |
| ST1964 (CD437) | 0.37 ± 0.02 | 12.7 ± 0.7 | 34 |
| ST2142 | 1.0 ± 0.06 | 2.2 ± 0.1 | 2.2 |
| ST1898 | 1.2 ± 0.02 | 64.4 ± 5.0 | 53.6 |
| ST3056 | 0.62 ± 0.04 | 1.2 ± 0.04 | 1.9 |
| ST3081 | 1.48 ± 0.19 | 1.39 ± 0.14 | 0.94 |
| ST2782 | 0.59 ± 0.07 | 1.80 ± 0.16 | 3.0 |
| ST3088 | 5.4 ± 0.3 | 7.5 ± 0.1 | 1.4 |

R.I. [RI = resistance index (IC50 on resistant tumour cell line/IC50 on sensitive tumour cell line)]

Cytodifferentiating Activity

Results

Acute promyelocytic leukemia (APL) is a form of acute myelogenous leukemia with typical chromosomal translocations leading to the expression of abnormal fusion proteins involving the nuclear retinoic acid receptor (RAR) α. These fusion proteins act as oncogenes and are responsible for the differentiation block and the expansion of the leukemic clone. In the majority of APL patients, the translocation involves chromosomes 15 and 17 and leads to the synthesis of promyelocytic leukemia (PML)-RARα. APL is the object of intense study, as it represents the only example of neoplastic disease that can be treated with a cytodifferentiating approach. APL patients are induced into clinical remission with all-trans retinoic acid (ATRA), which forces the leukemic blast to acquire many of the characteristics of the terminally differentiated neutrophils. These include a short lifespan and the propensity to undergo a natural process of programmed cell death or apoptosis.

Although the success obtained with APL patients has raised enthusiasm for the clinical use of ATRA in the treatment of leukemia and other neoplastic diseases, the therapeutic efficacy of this compound is still burdened by problems such as resistance and toxicity. One possible strategy to increase the therapeutic index of ATRA is the development of ATRA-based pharmacologic combinations that are more powerful and easily tolerated than the individual components.

Relevant aspects of the differentiation program set in motion by ATRA in APL cells can be reproduced in primary cultures of leukemic blasts and in the derived NB4 cell line, which is a unique model for the study of the pharmacologic activity of ATRA and derivatives. Pharmacological concentrations of ATRA arrest the growth of NB4 blasts and differentiate them into cells that resemble mature neutrophils. This is followed by a slow process of apoptosis. As reported in the Table 3, we used NB4 cells to demonstrate that such different compounds potentiate the pharmacologic activity of ATRA. In particular, the differentiation of NB4 tumour cells induced by the compounds was determined by nitroblue tetrazolium (NBT) reduction. NB4 promyelocytic leukaemia cells were seeded at a density of 150000 cells/ml in RPMI 1640 medium containing 10% FCS. To measure the cytodifferentiating effect of the molecules, tumour cells were treated with the compounds at different concentrations starting from at least 0.4 µM to 0.01 µM, whereas to measure the enhancing action of the molecules of ATRA activity, NB4 cells were treated with increasing concentrations of the molecules in the presence or absence of ATRA at a suboptimal concentration (5 nM).

Tumour cells were incubated for 3 days at 37° C. without replacing the medium culture. To measure the prodifferentiative effect, 500,000 cells were collected, centrifuged and resuspended in 1 ml of RPMI 1640 medium containing 10% FCS, 1 mg/ml of nitroblue tetrazolium (NBT) and 100 ng of PMA (4-phorbol-12-myristate-13-acetate). The tumour cells resuspended were incubated at 37° C. for 60 min. At the end of the incubation, tumour cells were centrifuged and the pellet was resuspended in 1 ml of PBS containing Triton ×100 at 10%. The samples were sonicated and the absorbance was determined at 540 nm with a spectrophotometer. Differentiation of tumor cells as AC50 (activating concentration) was evaluated as the concentration of the compound giving 50% of the maximal induction of NBT-reducing activity with or without ATRA. As shown in Table 4, the compounds alone were not able to induce differentiation of NB4 tumor cells, whereas when they were combined with a suboptimal concentration of ATRA (5 nM), some molecules increased ATRA-induced differentiation. The most potent compounds was ST2992 with an AC50 value of 0.19 μM comparable to ST2142 (AC50=0.31 μM) followed by ST2782 with AC50 values ranged from 2.47 μM.

Surprisingly, none of the closest analogues (ST1926, ST1964, ST3444, ST3256, ST3400) showed similar results.

TABLE 4

Enhancer effect of hydroxamic derivatives on cytodifferentiating activity of ATRA on NB4 tumour cells

| Compound | IC50 (μM ± SD) | Differentiation AC50 (μM) |
| --- | --- | --- |
| ST1926 | 0.082 ± 0.005 | no differentiation |
| ATRA + ST1926 | / | no differentiation |
| ST2992 | 0.68 ± 0.07 | no differentiation |
| ATRA + ST2992 | / | 0.19 ± 0.002 |
| ST1964 (CD437) | 0.4 ± 0.05 | no differentiation |
| ATRA + ST1964 (CD437) | / | no differentiation |
| ST2142 | 2.4 ± 0.08 | no differentiation |
| ATRA + ST2142 | / | 0.31 ± 0.04 |
| ST2782 | 2.3 ± 0.02 | no differentiation |
| ATRA + ST2782 | / | 2.47 ± 0.5 |
| ST3444 | 0.86 ± 0.05 | no differentiation |
| ATRA + ST3444 | / | no differentiation |
| ST3256 | 0.9 ± 0.1 | no differentiation |
| ATRA + ST3256 | / | no differentiation |
| ST3400 | 0.66 ± 0.003 | no differentiation |
| ATRA + ST3400 | / | no differentiation |

The invention claimed is:

1. A compound of Formula (I):

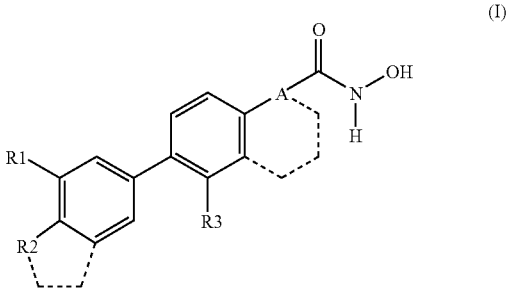

where:
   R1 is selected from the group consisting of H, adamantyl, Cl;
   R2 is selected from the group consisting of OMe, Cl, CN, and $(CH_2)_n OH$ where n is selected among 0, 1 and 2; or
   R2, taken together with the ring to which it is linked, it forms a methylene- or ethylene-dioxy derivative;
   R3 is selected from H and Cl;
   A is one of the following divalent groups: [CH═CH] (trans), and [C≡C].

2. The compound of Formula (I) of claim 1, which is selected form the group consisting of:
   E-3-(4'-hydroxy-biphenyl-4-yl)-N-hydroxy-acrylamide;
   E-3-[3'-(1-adamantyl)-4'-hydroxy-biphenyl-4-yl]-N-hydroxy-acrylamide;
   3-[4-(8-adamantan-1-yl-2,3-dihydrobenzo[1,4]dioxin-6-yl)-phenyl]-N-hydroxy-acrylamide;
   E-3-(3'-adamantan-1-yl-2-chloro-4'-hydroxy-biphenyl-4-yl)-N-hydroxy-acrylamide;
   E-3-(3'-adamantan-1-yl-4'-methoxy-biphenyl-4-yl)-N-hydroxy-acrylamide;
   E-3-(4'-hydroxy-biphenyl-4-yl)-N-hydroxy-propiolamide;
   E-3-(4'-hydroxymethyl-biphenyl-4-yl)-N-hydroxy-acrylamide;
   E-3-(3'-chloro-4'-hydroxy-biphenyl-4-yl)-N-hydroxy-acrylamide;
   E-3-[4'-methoxy-biphenyl-4-yl]-N-hydroxy-acrylamide;
   E-3-[4'-cyano-biphenyl-4-yl]-N-hydroxy-acrylamide; and
   E-3-[4'-chlorobiphenyl-4-yl]-N-hydroxy-acrylamide.

3. A pharmaceutical composition containing as active ingredient a compound according to claim 1, and at least one pharmaceutically acceptable excipient and/or diluent.

4. A process for preparing the composition according to claim 3 comprising mixing the active ingredient with at least one pharmaceutically acceptable excipient and/or diluent.

5. A method for the treatment of a tumour pathology, in which the tumour has shown drug resistance to other antitumour drugs used for the same treatment, wherein the tumour pathology is selected from the group consisting of colon cancer, ovarian cancer, non-small cell lung carcinoma, and leukaemia, comprising administering an effective amount of a compound of claim 1 to a mammal in need thereof.

6. The method according to claim 5, in which the tumour is selected from the group consisting of lymphoid leukaemia, acute promyelocytic leukaemia, myeloid leukaemia, monocytic leukaemia, and megakaryocytic leukaemia.

7. The method according to claim 6, in which the tumour is acute promyelocytic leukaemia.

8. The method according to claim 5 in which the compound is combined with one or more known antitumour agents.

9. The method according to claim 8, in which the known antitumour agent is all-trans retinoic acid.

* * * * *